US 6,558,328 B2

(12) United States Patent
Chiao et al.

(10) Patent No.: US 6,558,328 B2
(45) Date of Patent: May 6, 2003

(54) METHOD AND APPARATUS USING CODED EXCITATION IN ULTRASONIC PERFUSION IMAGING (75) Inventors: Richard Yung Chiao, Menomonee Falls, WI (US); Jonathan Matthews Rubin, Ann Arbor, MI (US); Kai Erik Thomenius, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 54 days.

(21) Appl. No.: 09/871,881

(22) Filed: Jun. 4, 2001

(65) Prior Publication Data

US 2001/0044278 A1 Nov. 22, 2001

Related U.S. Application Data (63) Continuation-in-part of application No. 09/757,762, filed on Jan. 11, 2001, now Pat. No. 6,491,631, and a continuation-in-part of application No. 09/494,465, filed on Jan. 31, 2000, now Pat. No. 6,375,618.

(51) Int. Cl.[7] ................................................. A61B 8/00
(52) U.S. Cl. ........................................................ 600/447
(58) Field of Search ................................ 600/437, 443, 600/447, 458–459

(56) References Cited

U.S. PATENT DOCUMENTS

| 5,014,712 A | 5/1991 | O'Donnell |
| 5,632,277 A | 5/1997 | Chapman et al. |
| 5,706,819 A | 1/1998 | Hwang et al. |
| 5,951,478 A | 9/1999 | Hwang et al. |
| 5,961,463 A | 10/1999 | Rhyne et al. |
| 5,980,459 A | 11/1999 | Chiao et al. |
| 5,984,869 A | 11/1999 | Chiao et al. |
| 6,010,456 A | 1/2000 | Rhyne |
| 6,050,947 A | 4/2000 | Rhyne et al. |
| 6,110,120 A * | 8/2000 | Holley et al. ............... 600/458 |
| 6,179,780 B1 * | 1/2001 | Hossack et al. ............ 600/437 |
| 6,213,947 B1 * | 4/2001 | Phillips ...................... 600/443 |
| 6,340,348 B1 * | 1/2002 | Krishnan et al. ........... 600/447 |

OTHER PUBLICATIONS

"Characteristics of Contrast Agents and 2D Imaging," de Jong et al., Proc. 1996 IEEE Ultrasonics Symposium, 1997, pp. 1449–1458.
"A New Imaging Technique Based on the Nonlinear Properties of Tissues," Averkiou et al., Proc. 1997 IEEE Ultrasonics Symposium, 1998, pp. 1561–1566.
"Coded Excitation for Harmonics Imaging," Takeuchi, Proc. 1996 IEEE Int'l Ultrasonics Symposium, 1997, pp. 1433–1436.
"Polyphase Complementary Codes," Frank, IEEE Trans. Inform. Theory, vol. IT–26, No. 6, Nov. 1980, pp. 641–647.

(List continued on next page.)

Primary Examiner—Francis J. Jaworski
(74) Attorney, Agent, or Firm—John F. Thompson; Patrick K. Patnode (57) ABSTRACT A method and an apparatus for perfusion imaging using coded excitation. Bursting pulses are scanned over the region of interest in one or more frames followed by scanning one or more encoded imaging pulses in each subsequent frame. The bursting pulse is intended to break contrast micro-bubbles within a transmit focal zone and therefore should have high mechanical index and low frequency. The basic concept is to use a very low-amplitude encoded pulse train to image the contrast agents. The low amplitude prevents the contrast bubbles in the transmit focal zone from being destroyed while imaging, and the coded excitation provides the necessary signal-to-noise ratio. The imaging pulses are transmitted during refilling of the transmit focal zone with contrast agent subsequent to transmission of the bursting pulse into the transmit focal zone. On receive, the receive vectors are decoded to form a compressed pulse.

33 Claims, 8 Drawing Sheets

OTHER PUBLICATIONS

"Multiphase Complementary Codes," R. Sivaswamy, IEEE Trans. Inform. Theory, vol. IT-24, No. 5, Sep. 1978, pp. 546-552.

"Coded Excitation System for Improving the Penetration of Real-Time Phased-Array Imaging Systems," M. O'Donnell, IEEE Trans. Ultrasonic Ferroelec. Freq. Cont., vol. 39, No. 3, May 1992, pp. 341-351.

"Transmit Aperture Processing for Non-Linear Contrast Agent Imaging," S. Krishnan; M. O'Donnell,Ultrasonic Imaging, vol. 18, 1996, pp. 77-105.

"Physics of Ultrasound Contrast Imaging: Scattering in the Linear Range," V. Uhlendorf, IEEE Trans. Ultrasonic Ferroelectrics & Frequency Control, vol. 41, No. 1, Jan. 1994, pp. 70-79.

"Principles and Recent Developments in Ultrasound Contrast Agents," N. de Jong; FJ Ten Cate; CT Lancee; JRTC Roelandt; N. Bom; Ultrasonics, vol. 29, 1991, pp. 324-330.

An Investigation of a Spread Energy Method for Medical Ultrasound Systems—Part Two: Proposed System and Possible Problems, Y. Takeuchi, Ultrasonic, vol. 17, Sep. 1979, pp. 219-224.

* cited by examiner

METHOD AND APPARATUS USING CODED EXCITATION IN ULTRASONIC PERFUSION IMAGING

CROSS REFERENCE TO RELATED APPLICATIONS

This application is a continuation-in-part of and claims the benefit of priority from U.S. patent application Ser. No. 09/494,465 filed on Jan. 31, 2000 now U.S. Pat. No. 6,375,618, and is also a continuation-in-part of and claims the benefit of priority from U.S. patent application Ser. No. 09/757,762 filed on Jan. 11, 2001 now U.S. Pat. No. 6,491,631.

BACKGROUND OF THE INVENTION

This invention generally relates to ultrasound imaging systems. In particular, the invention relates to methods and apparatus for imaging blood flow and contrast agents.

Conventional ultrasound transducers for use in medical diagnostic imaging transmit a broadband signal centered at a fundamental frequency $f_0$, which is applied separately to each transducer element making up the transmit aperture by a respective pulser. The pulsers are activated with time delays that produce the desired focusing of a transmit beam at a particular transmit focal position. As the transmit beam propagates through tissue, echoes are created when the ultrasound wave is scattered or reflected off of the boundaries between regions of different density. The transducer array is used to transduce these ultrasound echoes into electrical signals, which are processed to produce an image of the tissue. These ultrasound images are formed from a combination of fundamental (linear) and harmonic (nonlinear) signal components, the latter of which are generated in nonlinear media such as tissue or a blood stream containing contrast agents. With scattering of linear signals, the received signal is a time-shifted, amplitude-scaled version of the transmitted signal. This is not true for acoustic media which scatter nonlinear ultrasound waves.

The echoes from a high-level signal transmission will contain both linear and nonlinear signal components. In certain instances ultrasound images may be improved by suppressing the fundamental and emphasizing the harmonic (nonlinear) signal components. If the transmitted center frequency is at $f_0$, then tissue/contrast nonlinearities will generate harmonics at $kf_0$ and subharmonics at $f_0/k$, where k is an integer greater than or equal to 2. Imaging of harmonic signals has been performed by transmitting a narrow-band signal at frequency $f_0$ and receiving at a band centered at frequency $2f_0$ (second harmonic) followed by receive signal processing.

One fundamental problem faced by harmonic imaging is low harmonic-to-noise ratio (HNR) since the harmonic signals are at least an order of magnitude lower in amplitude than the fundamental signal. A secondary problem is insufficient isolation of the harmonic signal from the fundamental as measured by a low harmonic-to-fundamental ratio (HFR).

Coded Excitation is the transmission of long encoded pulse sequences and decoding of the received signals in order to improve image SNR and/or resolution. The energy contained in a long transmit pulse sequence is compressed into a short time interval on receive by virtue of the code. Coded excitation is a well-known technique in medical ultrasound imaging. For example, the use of Golay codes is disclosed in U.S. Pat. No. 5,984,869 issued on Nov. 16, 1999.

Likewise the technique of harmonic imaging using contrast agents is known.

Harmonic imaging images the nonlinear signal components produced inside the body that is used to enhance contrast agent signal when imaging blood flow. The technique of harmonic imaging using contrast agents is presented in de Jong et al., "Characteristics of Contrast Agents and 2D Imaging," Proc. 1996 IEEE Intl Ultrasonics Symp., pp. 1449–1458 (1997). Contrast harmonics can greatly improve vascular studies.

Harmonic imaging that uses two transmits with 180-degree phase shifts has been disclosed. The pulse inversion between the two transmits suppresses the fundamental signal and leaves the harmonic signal to form the image. Harmonic coded excitation that uses pulse sequences with 0 and 90-degree phase symbols (e.g., "1" and "j", where $j^2=-1$) has been disclosed by Takeuchi in "Coded Excitation for Harmonic Imaging," Proc. 1996 EEE Intl Ultrasonics Symp., pp. 1433–1436 (1997) and by Chiao et al. in U.S. patent application Ser. No. 09/494,465 filed on Jan. 31, 2000. However, a method to suppress the fundamental signal on reception was not specified in those disclosures. Harmonic coded excitation using Quadrature Phase Shift Keying (QPSK) (i.e., symbols 1, –1, j and –j) with suppression of the fundamental signal on reception was disclosed in U.S. Pat. No. 6,050,947 issued on Apr. 18, 2000.

It is known to use ultrasound imaging systems to image perfusion in an anatomical region. Perfusion imaging provides an assessment of rate of blood flow in the anatomical region and is useful for diagnosis of pathological conditions such as myocardial ischemia, tumor diagnosis, and transplant evaluations. Because much of perfusion occurs in micro-capillaries, perfusion imaging requires the ability to distinguish low-speed flow from tissue. The problem is exacerbated by the small diameter of the capillaries which limits the echo strength from the blood and thus the signal-to-noise ratio (SNR). Conventional flow imaging that uses color or power Doppler is unable to surmount these problems and is ineffective for perfusion imaging.

Recent advances in contrast agents have opened the door to perfusion imaging. Contrast agents are typically encapsulated gas micro-bubbles between 0.1 micron and 10 microns in diameter. When introduced into the body by injection, contrast agents serve as high-reflectivity markers for blood flow and perfusion. Ultrasound energy incident on the micro-bubbles is strongly reflected at the incident (fundamental) frequencies and at the harmonic frequencies. Because the ratio of contrast agent-generated signal to tissue-generated signal is much larger for harmonic signal components than for the fundamental signal components, the harmonic signal components are preferred for perfusion imaging.

There are several prior art methods for perfusion imaging. Methods have been investigated that destroy bubbles in feeding vessels in such a way that a near impulse input, which corresponds to a nearly perfect bolus, is generated. Tracking the passage of the impulse through a tissue region gives the tissue response function from which perfusion can be calculated. Another potential method employs speckle decorrelation to estimate the local mean transit time through tissue. The mean transit time along with an estimate of the fractional blood volume would produce an estimate of perfusion. In a third prior art technique, the sampled perfusion method, a sequence of bursting and imaging pulses are transmitted with varying time intervals. The bursting pulses destroy the contrast micro-bubbles within the region of interest while the imaging pulses measure the amount of contrast agent refill that has occurred over that time interval. The perfusion curve over time is measured by using multiple pairs of bursting and imaging pulses with varying intervals. The drawback of this method is that the perfusion curve is built up slowly and extra contrast agent may be required as contrast bubbles are repeatedly cleared and refilled within the region of interest. Finally, a continuous perfusion method uses low-mechanical-index (i.e., low-amplitude) imaging pulses that do not burst contrast bubbles. In this method, the bursting pulse is used only once, followed by imaging pulses that measure the refill at each time instant. This method provides real-time perfusion imaging, but suffers from low SNR because of the low-mechanical-index imaging pulses that are used.

There is a need for a method of real-time imaging of perfusion in an anatomical region that provides improved SNR.

BRIEF SUMMARY OF THE INVENTION

The present invention is directed to a method and an apparatus for providing perfusion images having improved SNR using coded excitation in conjunction with the continuous perfusion method. Coded excitation is the transmission of long encoded pulse trains and decoding of the received signals in order to improve image SNR. Specifically, the energy contained in the long transmit pulse train is compressed into a short time interval on receive by virtue of the code.

The method in accordance with the preferred embodiments of the invention comprises the steps of bursting contrast micro-bubbles (using either a very large bursting pulse or by scanning a smaller bursting pulse) in the region of interest in one or more frames followed by scanning one or more encoded imaging pulses in each subsequent frame. The bursting pulse (or pulses) is intended to break contrast micro-bubbles within a region and therefore should have high mechanical index and low frequency. The basic concept is to use a very low-amplitude, focused, encoded pulse train (hereinafter "imaging pulses") to image contrast agents. The low amplitude prevents the contrast bubbles in the transmit focal zone from being destroyed while imaging, and the coded excitation provides the necessary SNR. The imaging pulses are transmitted during refilling of the transmit focal zone with contrast agent subsequent to transmission of the bursting pulse into the same zone.

In accordance with the preferred embodiments, QPSK-encoded imaging pulses centered at a fundamental frequency and focused in the transmit focal zone are transmitted. In a one-transmit embodiment, the imaging pulse waveform is encoded such that the received second harmonic signal will be encoded with a Barker code. In a two-transmit embodiment, the imaging pulse waveforms are encoded such that the respective received second harmonic signals are encoded with respective Golay codes of a Golay code pair. A Golay code pair X and Y satisfies the complementarity property $X^* \underline{X} + Y^* \underline{Y} = \delta(n)$, where the "*" symbol denotes convolution and $\delta(n)$ is a Kronecker delta function. In a four-transmit embodiment, a different QPSK transmit code is used for each of four transmits A, B, C and D. The transmit codes are selected such that (A−B) and (C−D) are encoded by Y and $-\underline{X}$, respectively, while $(A^2-B^2)$ and $(C^2-D^2)$ are encoded by X and Y, respectively, where X and Y form a Golay code pair. X is a sequence such that X=x(n), n=0, 1, 2, . . . , (N−1), and $\underline{X}$ denotes the reversal of X given by $\underline{X}$=x(N−1−n) for n=0, 1, 2, . . . , (N−1). The same is true for Y and $\underline{Y}$.

In the two- and four-transmit embodiments, the encoded pulses (transmitted at different times) are focused at the same transmit focal position. This is repeated for each transmit focal position in the scanning plane. The resulting receive vectors are decoded to form a compressed pulse vector. The fundamental signal components are suppressed while the second harmonic signal components are fully compressed in the decoded waveform. The evolution of brightness at registered points in a sequence of image frames indicates the change in contrast agent concentration or perfusion at those points.

DETAILED DESCRIPTION OF THE INVENTION

Figure 1:
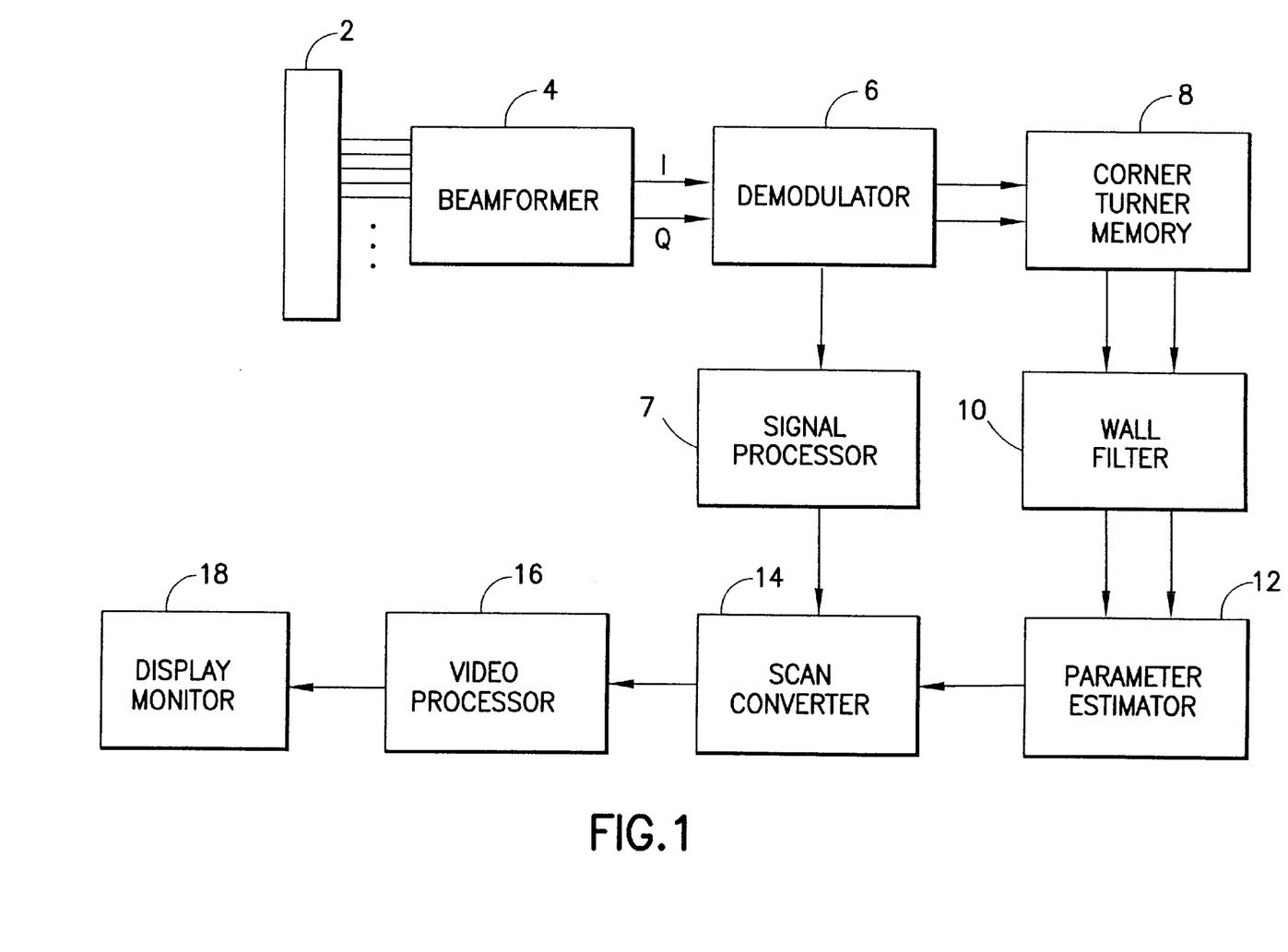
FIG. 1 is a block diagram showing a conventional ultrasound imaging system.

A conventional ultrasound imaging system having B mode and color flow mode is generally depicted in FIG. 1. The system comprises a transducer array 2 consisting of a plurality of separately driven transducer elements, each of which produces a burst of ultrasonic energy when energized by a pulsed waveform produced by a transmitter in beam former 4. The ultrasonic energy reflected back to transducer array 2 from the object under study is converted to an electrical signal by each receiving transducer element and applied separately to a receiver channel in beamformer 4. The transmitter and receiver are operated under control of a host computer or master controller (not shown). The beamformer 4 combines the separate echo signals from each transducer element to produce a single echo signal which is used to produce a line in an image on a display monitor 18.

On receive, the beamformer 4 performs analog-to-digital conversion and receive beamforming. In baseband imaging systems, the beamsummed signal is output to a demodulator 6, which converts the beamsummed signal into baseband in-phase I and quadrature Q receive beams. The I and Q acoustic data vectors from the demodulator 6 are sent to respective FIR filters (not shown), which are programmed with filter coefficients to pass a band of frequencies preferably centered at the fundamental frequency $f_0$ of the transmit waveform or a (sub)harmonic frequency thereof.

In the case of a B-mode imaging system, vectors of filtered I and Q acoustic data are sent to a B-mode signal processor 7, which converts the I and Q acoustic data into a log-compressed version of the signal envelope. The B-mode function images the time-varying amplitude of the envelope of the signal as a gray scale. The envelope of a baseband signal is the magnitude of the vector which I and Q represent. The I,Q phase angle is not used in the B-mode display. The magnitude (i.e., intensity) of the signal is the square root of the sum of the squares of the orthogonal components, i.e., $(I^2+Q^2)^{1/2}$.

The B-mode amplitude data is output to a scan converter 18 comprising an acoustic line memory followed by an X-Y display memory. The acoustic line memory accepts the processed vectors of amplitude data and interpolates where necessary, and also performs the coordinate transformation of the amplitude data from polar coordinate (R–θ) sector format or Cartesian coordinate linear format to appropriately scaled Cartesian coordinate display pixel intensity data, which is stored in the X-Y display memory.

The scan-converted frames are passed to a video processor 20, which converts the pixel intensity data to the video frame rate and then maps the pixel intensity data to a gray-scale mapping for video display. A conventional ultrasound imaging system typically employs a variety of gray maps, which are simple transfer functions of the raw intensity data to display gray-scale levels. The gray-scale image frames are then sent to the display monitor 22 for display.

FIG. 1 also shows the basic signal processing chain for the color flow mode. The transducer array 2 is activated to transmit coded pulse sequences comprising phase-coded tone bursts of length P which are fired repeatedly at the PRF. The return RF signals are detected by the transducer elements and received by the respective receive channels in the beamformer 4. The beamformer sums the delayed channels data and outputs either RF or in-phase and quadrature (I/Q) data. The latter alternative is illustrated in FIG. 1.

In the system shown in FIG. 1, the frequencies of the beamformer outputs are shifted to baseband by the demodulator 6. The demodulated I/Q components are stored in a corner turner memory 8, whose purpose is to buffer data from possibly interleaved firings and output the data as vectors of points across firings at a given range cell. Data is received in "fast time", or sequentially down range (along a vector) for each firing. The output of the corner turner memory is reordered into "slow time", or sequentially by firing for each range cell. The resultant "slow time" I/Q signal samples are passed through respective wall filters 10, which reject any clutter corresponding to stationary or very slow-moving tissue. The filtered outputs are then fed into a parameter estimator 12, which processes the magnitude and phase values into estimates of power, velocity and turbulence.

The color estimates are sent to the scan converter 14, which converts the color images into X-Y format for video display. The scan-converted frames are passed to a video processor 16, which basically maps the video data to a display color map for video display. The color flow image frames are then sent to the video monitor 18 for display. Typically, either velocity or power are displayed alone or velocity is displayed in conjunction with either power or turbulence.

System control is centered in a control computer (25 in FIG. 3), which accepts operator inputs through an operator interface (not shown) and in turn controls the various subsystems, as will be explained in detail hereinafter.

Figure 2:
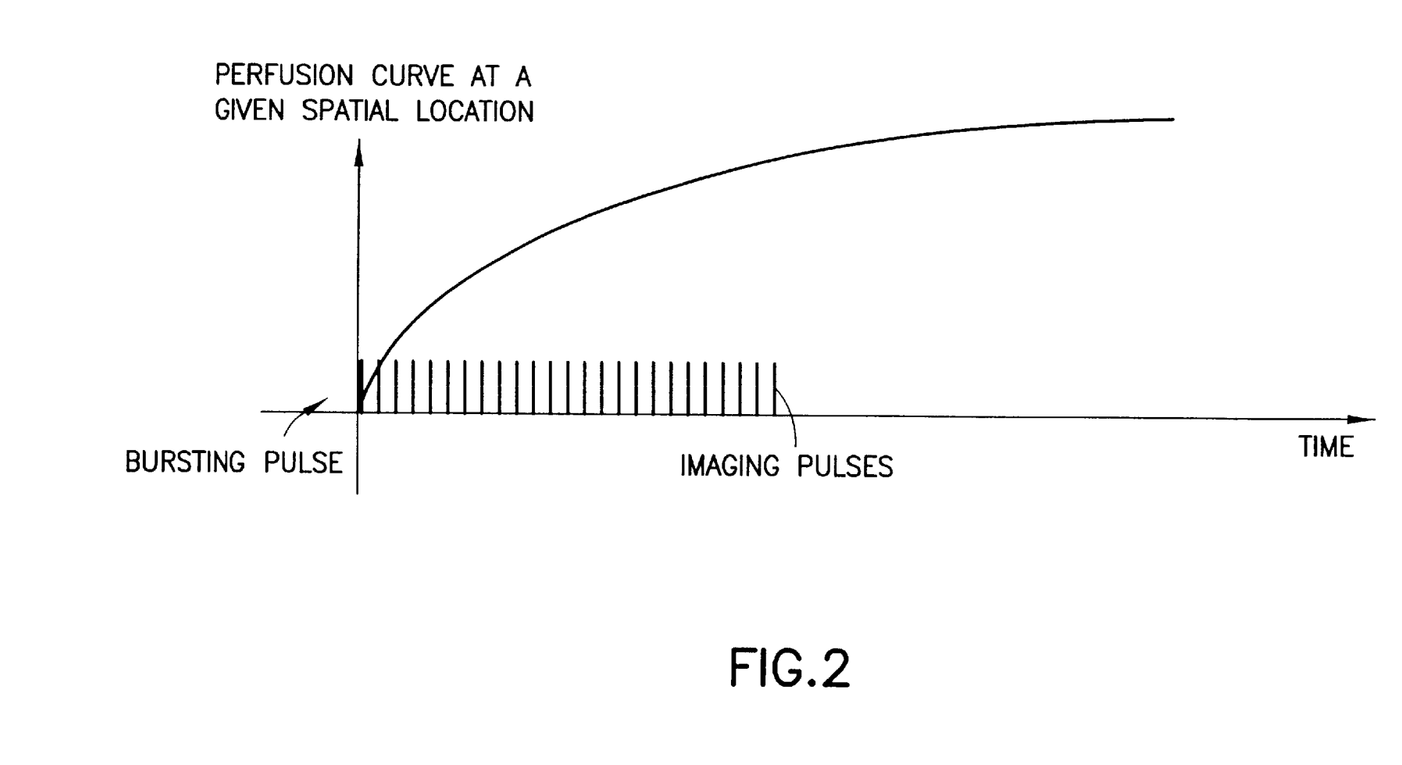
FIG. 2 is a graph showing a perfusion curve at a given spatial location, measured using a sequence of imaging pulses transmitted to that spatial location following transmission of a bursting pulse in accordance with the preferred embodiments of the invention. Depending on the embodiment, each vertical line represents either one encoded imaging pulse, a packet of two encoded imaging pulses, or a packet of four encoded imaging pulses.

The system depicted in FIG. 1 can be programmed to perform continuous perfusion imaging, as is generally depicted in FIG. 2. Continuous perfusion imaging uses low-MI imaging pulses that do not burst contrast bubbles. In this method, a bursting pulse is transmitted to a focal zone followed by imaging pulses that measure the refill at each time instant at the same location. In accordance with the preferred embodiments of the invention, each vertical line in FIG. 2 represents either one encoded imaging pulse, a packet of two encoded imaging pulses, or a packet of four encoded imaging pulses, all focused at the same position where the bursting pulse was focused.

The imaging method in accordance with the preferred embodiments comprises the following steps. First, contrast micro-bubbles are injected into an anatomical region of the patient. Then selected transducer elements are activated to transmit a bursting pulse waveform into a transmit focal zone located within the aforementioned anatomical region. The bursting pulse waveform has an amplitude sufficient to burst contrast micro-bubbles in the transmit focal zone. After trans-mission of the bursting pulse waveform, selected transducer elements are activated to transmit at least one QPSK-encoded imaging pulse waveform. Each imaging pulse waveform is focused in the transmit focal zone. Following each imaging pulse waveform transmission, the transducer elements detect the returning wave energy and output analog electrical signals. The receiver forms a respective receive vector from these electrical signals subsequent to each transmission of an encoded imaging pulse waveform. The receive vector(s) is/are decoded to form a compressed second-harmonic pulse vector, with the fundamental signal components being at the same time suppressed. Ultimately, a perfusion image is displayed having an image portion which is a function of the compressed pulse vector.

Figure 3:
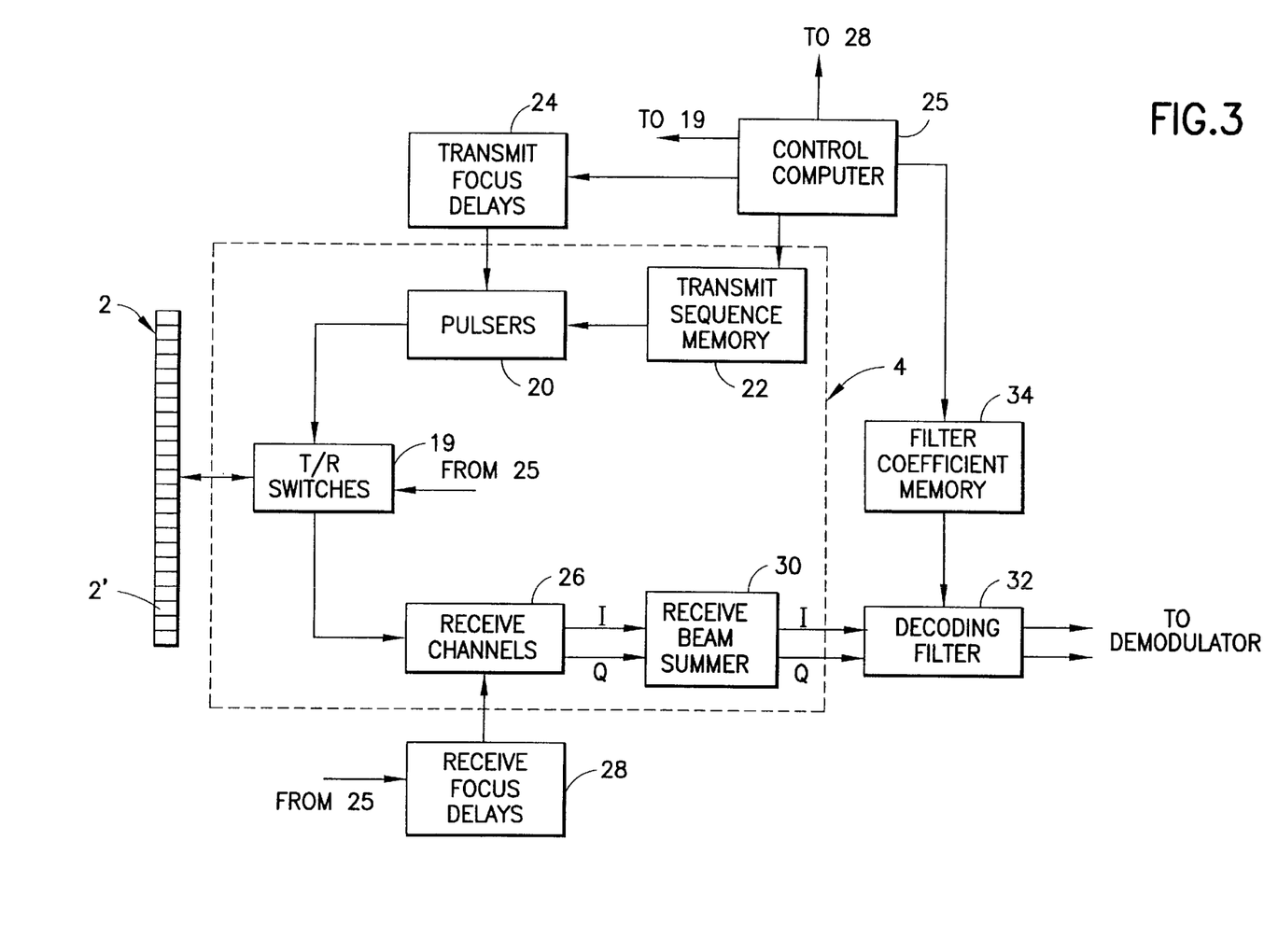
FIG. 3 is a block diagram showing an ultrasound imaging system in accordance with the preferred embodiments of the invention.

FIG. 3 generally depicts a system for transmitting a bursting pulse waveform followed by an encoded imaging pulse waveform, with the second-harmonic receive signal resulting from the imaging pulse waveform being decoded to form a compressed second-harmonic pulse, thereby improving the SNR and/or resolution of the perfusion image. During the imaging transmit, each transducer element 2' in the transmit aperture is pulsed with a QPSK-encoded pulse sequence output by a respective multiphase pulser 20. The coded pulse sequence is derived from a coded transmit sequence formed by convolving a QPSK transmit code with a base sequence (e.g., a tone burst). The QPSK-encoded transmit sequence for controlling the phase of pulses output by each multiphase pulser 20 is stored in a transmit sequence memory 22 by a control computer 25, which also controls and synchronizes the beamforming and decoding functions.

The multiphase pulsers 20 drive the elements 2' of transducer array 2 such that the ultrasonic energy produced is focused in a beam for each transmit firing. To accomplish this, transmit focus time delays 24 (e.g., provided by the control computer 25) are imparted to the respective pulsed waveforms output by the pulsers in response to the coded transmit sequence. By appropriately adjusting the transmit focus time delays in a conventional manner, the ultrasonic beam can be focused at a desired transmit focal position. The coded pulse sequences are sent from the pulsers to the transducer elements via respective transmit/receive (T/R) switches 19. The control computer 25 also preferably control the state of the T/R switches, i.e., transmit versus receive.

After each transmit, the T/R switches 19 are switched to receive mode to accept the signals output by the transducer elements in response to returning echoes backscattered from the object being scanned. These return signals are fed to respective receive channels 26 of the receive beamformer. The receive beamformer tracks echoes under the direction of a master controller (not shown). The receive beamformer imparts the proper receive focus time delays 28 (preferably provided by the control computer 25) to the received echo signal and sums them to provide an echo signal which accurately indicates the total ultrasonic energy reflected from a succession of ranges corresponding to a particular transmit focal position. In accordance with the embodiment depicted in FIG. 3, the beamformer also transforms the RF signal into its I/Q components by means of Hilbert bandpass filtering in each receive channel. The I/Q components are then summed in receive summer 30 for each transmit firing. Hilbert bandpass filtering can alternatively be performed after beam summation. The I/Q components for each transmit of an encoded imaging pulse waveform are then decoded by a respective decoding filter 32 which outputs a compressed pulse.

FIG. 3 shows a preferred embodiment of the invention employing single-transmit coded excitation for the display of a harmonic image. In this system each transducer element in the transmit aperture is pulsed using a QPSK-encoded base sequence. The encoded base sequence is formed by convolving a base sequence (comprising a sequence of +1 and −1 elements) with an oversampled code sequence (comprising an n-digit code, each digit being either of two code symbols, +1 and −1). In particular, the base sequence is phase encoded, using an n-digit code sequence, to create an n-chip encoded base sequence which is stored in a transmit sequence memory 22. For single-transmit codes (e.g., Barker codes), the transmit sequence memory 22 stores one encoded base sequence for each transmit focal zone. For two-transmit codes (e.g., Golay codes), the transmit sequence memory 22 stores two encoded base sequences for each transmit focal zone. A similar rule applies to codes having more than two transmits.

Figure 4:
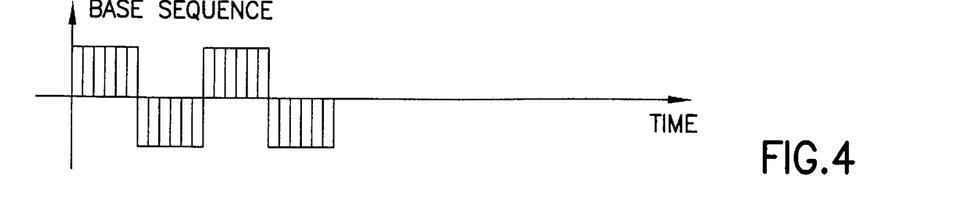
FIGS. 4–7 are pulse diagrams showing a base sequence (FIG. 4), an oversampled code sequence (FIG. 5), an encoded transmit sequence for fundamental imaging (FIG. 6), and a QPSK-encoded transmit sequence for harmonic imaging (FIG. 7).
Figure 5:
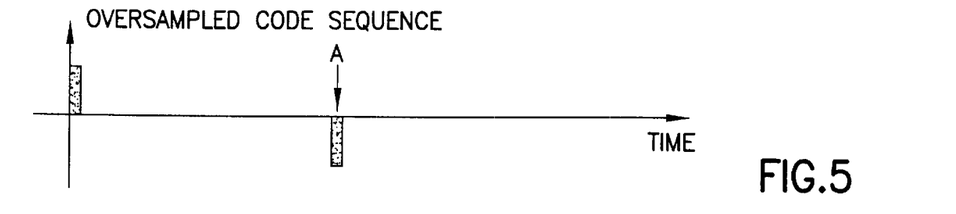
Figure 6:
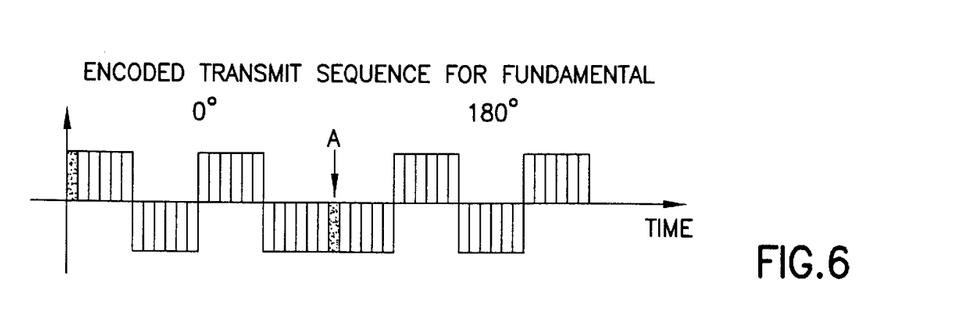
Figure 7:
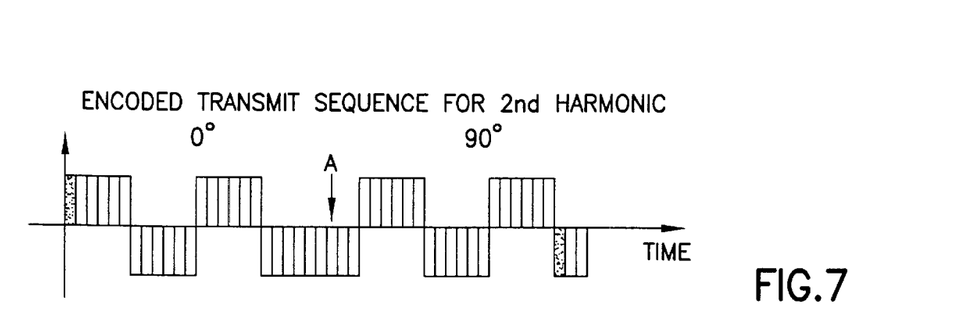

The generation of an exemplary encoded base sequence for use in harmonic imaging in accordance with a preferred embodiment of the invention is shown in FIGS. 4, 5 and 7. For comparison, FIG. 6 shows the corresponding encoded base sequence for use in conventional imaging of the fundamental signal components. In the latter case, the code sequence is transmitted not directly but by first oversampling (typically at 40 MHz or d=0.025 $\mu$sec time samples) and then convolving the oversampled code sequence (shown in FIG. 5) with a base sequence (shown in FIG. 4) to form the encoded base sequence (see FIG. 6). The start of the base sequence encoded with the second code symbol of the code sequence is designated by the letter "A" in FIGS. 6 and 7. The encoded base sequence can be transmitted much more efficiently since its spectrum is better matched to the transducer passband with proper selection of the base sequence.

Conventional biphase codes, such as Barker and Golay codes, have two phase-inverted symbols such as +1 and −1. However, to encode the transmit waveform for acquiring the N-th harmonic signal using the code symbols of the code sequence shown in FIG. 5, the chips of the transmit waveform encoded with the second code symbol (i.e., −1) need to be phase-shifted by 180°/N relative to the chips encoded with the first code symbol (i.e., +1). This is because if the transmitted signal has a phase term exp[j$\theta$], then the received N-th harmonic signal has a phase term exp[jN$\theta$]. In particular, to encode the transmit waveform for acquiring the second (N=2) harmonic signal, the respective chips corresponding to the two code symbols +1 and −1 must be 90° apart (as shown in FIG. 7) in order for the respective second harmonic receive signals to be 180° apart. On receive, the fundamental signal is suppressed and the second harmonic signal is decoded, i.e., compressed.

The phase shift in the encoded base sequence corresponding to the second code element is implemented by circularly shifting the corresponding chip in time by T=1/(2N$f_0$) $\mu$sec, where N is the harmonic order and $f_0$ is the fundamental (i.e., transmit) center frequency in MHz. For example, for N=2 (second harmonic) and $f_0$=3.33 MHz, the time shift is T=0.075 $\mu$sec, which corresponds to T/dt=3 time samples. The chip in the encoded base sequence corresponding to a 90° phase shift is then circularly shifted in time by three time samples, the first of the 3 shifted time samples being shaded in FIG. 7. This is implemented by circularly shifting the second encoded base sequence (i.e., chip) by a quarter cycle in the transmit sequence memory.

Each encoded base sequence read out of transmit sequence memory 22 controls activation of a multiplicity of pulsers 20 during a respective transmit firing. The encoded base sequence for a given focal position is transmitted with sufficient amplitude such that harmonic signals are generated from nonlinear propagation in tissue. The pursers 20 drive the elements 2' of transducer array 2 such that the ultrasonic energy produced is focused in a beam for each transmit firing. To accomplish this, transmit focus time delays 24 are imparted to the respective pulsed waveforms output by the pulsers. By appropriately adjusting the transmit focus time delays in a conventional manner, the ultrasonic beams can be focused at a multiplicity of transmit focal positions to effect a scan in an image plane.

For each transmit, the echo signals from the transducer elements 12 are fed to respective receive channels 26 of the receive beamformer. Each receive channel has a TGC amplifier and an analog-to-digital converter (not shown in FIG. 3). Under the direction of the control computer 25, the receive beamformer tracks the direction of the transmitted beam. The receive beamformer memory 28 imparts the proper receive focus time delays to the received echo signal and the receive beam summer 30 sums them to provide an echo signal which accurately indicates the total ultrasonic energy reflected from a particular transmit focal position. The time-delayed receive signals are summed in receive beam summer 30 for each transmit firing.

For single-transmit coded excitation, the beamsummed receive signals acquired following the transmit firing are output to a decoding filter 32, which correlates the beam-summed receive signal with a receive code. Preferably, the decoding filter 32 comprises a finite impulse response (FIR) filter. Suitable filter coefficients are stored in memory 34 and are output to decoding filter 32 at the appropriate times. The FIR filter will have filter coefficients a(n) which are a function of the transmit code, where n=0, 1, 2, . . . , (N−1).

The decoded receive signal is demodulated by demodulator 6 (see FIG. 1) and output to the signal processor 7. In the B mode, signal processing includes envelope detection, edge enhancement and logarithmic compression. After signal processing and scan conversion, a scan line is displayed on the display monitor. This procedure is repeated so that a respective scan line is displayed for each transmit focal position (in the case of one transmit focal position for each beam angle) or for each vector (in the case of multiple transmit focal positions for each beam angle), thereby forming a harmonic image of the desired order.

In the case of single-transmit codes, the QPSK encoding is specially designed to produce a second-harmonic signal on receive comprising an encoded sequence of n chips. The output from the beamformer is compressed in time by passing it through the decoding filter 32 (see FIG. 3). Some coded waveforms are best compressed by matched filtering, i.e., using a set of decode FIR filter coefficients a(n) that is an identical copy of the n-chip second-harmonic receive signal. However, sometimes more desirable compression effects are achieved by mismatched filtering using FIR filters that have more than n filter coefficients or have coefficients which differ from the n-chip second-harmonic receive signal. The output of the decoding filter 32 is a compressed-pulse second-harmonic signal.

Figure 8:
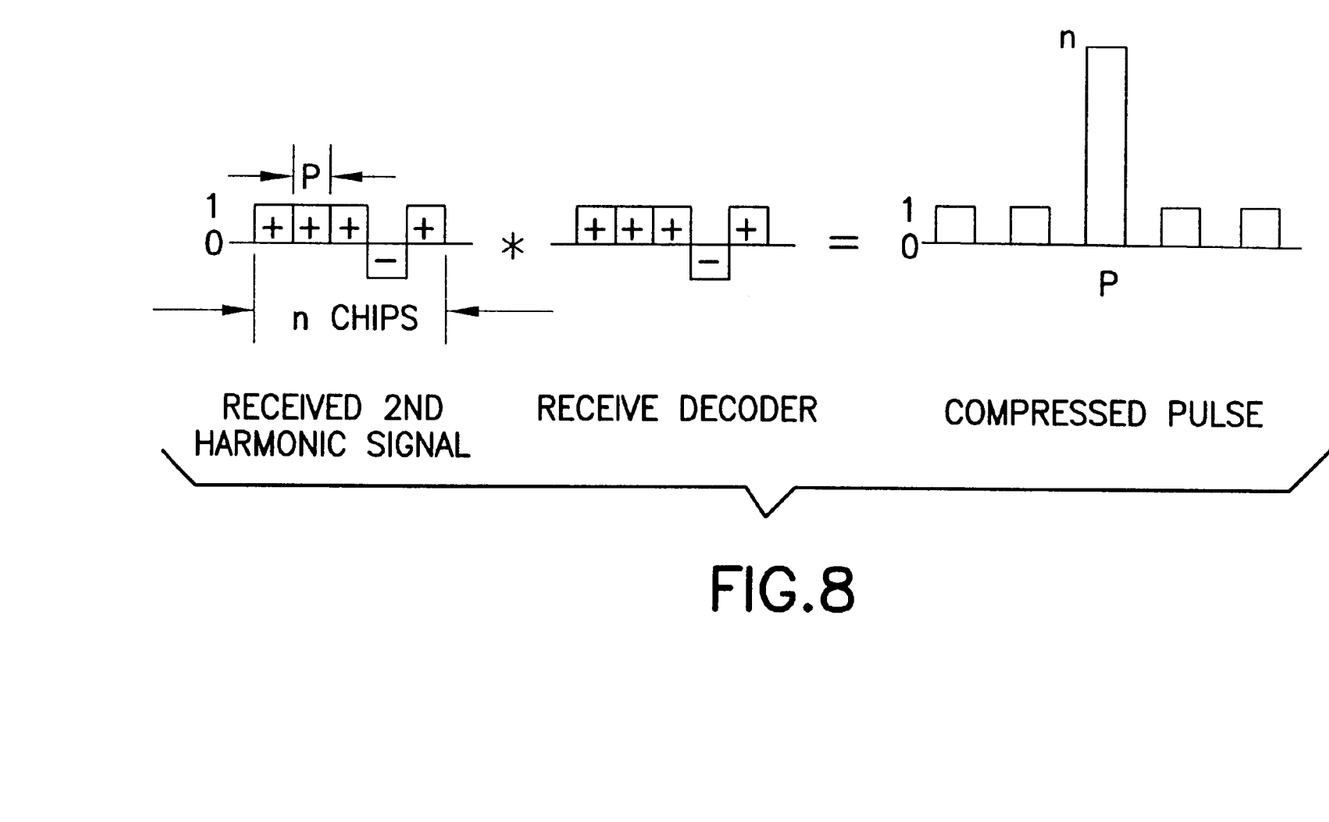
FIG. 8 is a schematic illustrating a compressed pulse resulting from convolution of a 5-bit received second harmonic signal with matched filter coefficients of a decoding filter in accordance with another preferred embodiment of the invention.

As an example, FIG. 8 shows a second-harmonic receive signal comprising a 5-chip code sequence from the Barker code family. Barker codes are biphase (or binary) code sequences of various lengths up to n=13. [The set of all Barker codes is disclosed in an article by Welch et al. entitled "Sidelobe suppressed spread spectrum pulse compression for ultrasonic tissue imaging," IEEE Trans. Ultrasonics, Ferroelec., and Freq. Control (accepted for publication, August 1997).] If the 5-bit Barker code [1,1,1, −1,1] is decoded by a matching FIR filter (i.e., a filter having filter coefficients identical to the digits of the Barker code) as shown in FIG. 8, the compression ratio achieved is n=5, which corresponds to a SNR gain of 7 dB. However, as seen in FIG. 8, the main pulse in the decoder filter output is surrounded by pulses of smaller amplitude. These small-amplitude pulses correspond to axial or range sidelobes that are 1/n times lower in amplitude compared to the main lobe.

The decoding or autocorrelation is achieved on receive by the decoding filter.

The appropriate decoding filter is designed based on the Barker code, the demodulation frequency (if decoding follows demodulation) and the amount of downsampling performed on receive.

Among all biphase codes, Barker codes are well known for their property of having the smallest sidelobes possible when decoded by a matched filter. However, it should be noted that for any single-transmit code, the sidelobes can often be suppressed via mismatched filtering at the expense of decreased signal gain and/or main lobe broadening (decreased range resolution). By using fewer or more taps for the mismatched filter, the sidelobes can be increased or decreased, resulting in a decrease or increase in peak signal loss. In general, greater sidelobe suppression can be achieved using longer mismatched FIR filters.

Figure 9:
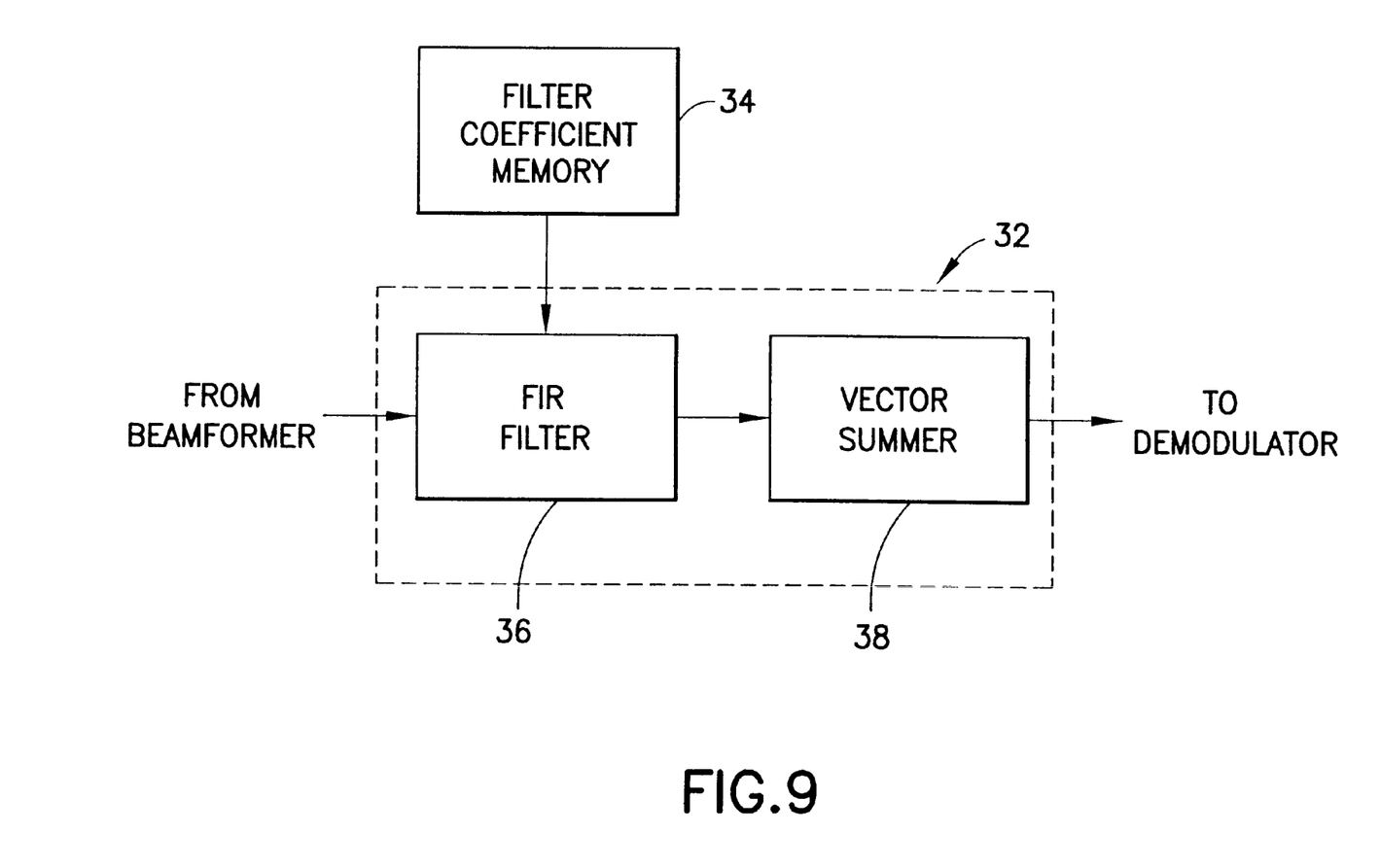
FIG. 9 is a block diagram showing the general structure of a decoding filter used in preferred embodiments of the invention which transmit multiple encoded imaging pulse waveforms to each transmit focal zone.

For two-transmit codes (e.g., Golay), there are two QPSK-encoded base sequences for each transmit focal zone. The encoded base sequences for a given focal position are transmitted with sufficient amplitude such that harmonic signals are generated from nonlinear propagation in tissue, and the received waveforms are beamformed, decoded, and used to form a harmonic image. For two-transmit codes, the decoding filter 32 comprises an FIR filter 36 and a vector summer 38, as seen in FIG. 9. The output of the FIR filter 36 is accumulated over the two transmits at a given focal position to complete the decoding step. For the purpose of this application, the term "decoder" means hardware and/or software for performing the functions of compressing and summing the respective harmonic signal components.

In the case of the two-transmit embodiment depicted in part in FIG. 9, the FIR filter 36 and the vector summer 38 form a decoder. During reception following the first QPSK-encoded transmit, the FIR filter 36 filters a first beam-summed receive vector in accordance with a first set of filter coefficients which are matched to the first Golay code. The first filtered receive vector output by filter 36 is then stored in a buffer memory in a vector summer 38. During reception following the second QPSK-encoded transmit, the FIR filter 36 filters a second beamsummed receive vector in accordance with a second set of filter coefficients which are matched to the second Golay code. The second filtered receive vector is output to the vector summer 38, where it is summed with the first filtered receive vector stored in buffer memory. The resulting summed vector is then further processed for image display.

In the case of two-transmit coded excitation, the transducer elements are pulsed in accordance with a first coded sequence during a first transmit firing focused at a desired transmit focal position and in accordance with a second coded sequence during a second transmit firing focused at the same transmit focal position. The first and second coded sequences are generated by respectively convolving first and second code sequences (e.g., Golay code pairs) with the base sequence, i.e., by phase encoding the base sequence using the code sequences. In accordance with a preferred embodiment, the first and second transmit codes are complementary Golay codes, e.g., the Golay code pair [1,1] and [1,−1]. For N-th harmonic imaging, each chip of the Golay-encoded base sequences which is encoded by the code symbol −1 is time shifted by ½N fractional cycle relative to the chips encoded by the code symbol +1.

During each firing, pulsers 20 are excited by a QPSK-encoded base sequence output from transmit sequence memory 22 or from specialized hardware. In response to the QPSK-encoded base sequence from transmit sequence memory 22 and the transmit focus delays output from lookup table 24, the pulsers 20 output QPSK-encoded pulse sequences to the respective transducer elements 2' making up the transmit aperture.

For each firing, decode filtering is performed using the oversampled Golay sequence corresponding to the Golay code used to generate the QPSK-encoded base sequence that was transmitted. The time-reversed oversampled Golay sequences are stored in the filter coefficient memory 34 and are output to filter 36 (see FIG. 9) at the appropriate times. Preferably, the filter 36 is a finite impulse response filter which performs the correlation:

$$x(n) * \overline{y(-n)} = \sum_m x(m+n)\overline{y(m)}$$

where * denotes convolution and the overbar denotes conjugation (if x and y are complex). The results of the correlations are summed in vector summer 38 to form the decoded signal, which is then output to the demodulator.

The imaging system incorporating the structure shown in FIG. 9 can also operate by demodulating the RF echo signals to baseband and downsampling before or after beam summation. In this case, the oversampled Golay sequences that are stored for correlation would also be demodulated to baseband and downsampled.

The FIR filter can be implemented in software or hardware at the beamformer output, as shown in FIG. 3, or at the demodulator output (not shown). In the latter case, the FIR filter coefficients must be matched or mismatched to the demodulated signals. For the case when the demodulator shifts by discrete frequencies $f_d=k/2t_b$, where k is any positive integer and $t_b$ is the duration of the encoded base sequence, the sinusoidal becomes real and the same set of filter coefficients are input to both composite filters for the I and Q components, which thus form a real filter. In the cases when $f_d \neq k/2t_b$, the I and Q composite filters receive different sets of filter coefficients and thus form a complex filter. In the latter case, the filter coefficients are either matched or mismatched to the respective demodulated signal component. The filter coefficients, like the transmit and receive time delays and the coded transmit sequences, can be supplied by the control computer 25 (see FIG. 3).

For four-transmit coded excitation, the beamsummed receive signals acquired following each transmit firing are output to a matched filter 36 (see FIG. 9), which convolves each beamsummed receive signal with a respective receive code. Preferably, the matched decoding filter 36 comprises a finite impulse response (FIR) filter. Suitable filter coefficients are stored in memory 34 and are output to matched filter 36 at the appropriate times.

In accordance with the preferred embodiment for harmonic imaging, the beamsummed receive signals from first through fourth successive firings are output to the matched filter 36, which convolves the first beamsummed receive signal with a first receive code for the first transmit firing, the second beamsummed receive signal with a second receive code for the second transmit firing, and so forth. The match-filtered signals derived from the first through fourth transmit firings focused at the same transmit focal position are summed in vector summer 38. The matched filter 36 and vector summer 38 together perform pulse compression of the harmonic signal and suppression of the fundamental signal.

In the case of four-transmit coded excitation in accordance with a preferred embodiment of the invention, the transmit sequences are generated using QPSK implemented as quarter-cycle circular rotations or shifts of the base pulse. The QPSK transmit code symbols are "1", "−1", "j" and "−j". The QPSK is implemented by time shifting the chips of the transmit sequence encoded with a "j" or "−j" code symbol by ¼ fractional cycle at center frequency relative to the chips encoded with a "1" or "−1" code symbol, as demonstrated in FIG. 7. For the code symbol "1", for example, one can transmit the base pulse [1,1, −1, −1], which implies that the phase-inverted base pulse [−1, −1, 1, 1] would correspond to the "−1" symbol. One can further assign the right quarter-cycle rotation of the base pulse [−1, 1, 1, −1] to be the "j" symbol, which then implies that the "−j" symbol would be the left quarter-cycle rotation [1, −1, −1, 1].

In accordance with the preferred embodiments of the invention, a different QPSK transmit code is used for each of four transmits A, B, C and D. The transmit codes are selected such that (A−B) and (C−D) are encoded by $\underline{Y}$ and $-\underline{X}$, respectively, while $(A^2-B^2)$ and $(C^2-D^2)$ are encoded by X and Y, respectively, where X and Y form a Golay code pair, X is a sequence such that X=x(n), n=0, 1, 2, ..., (N−1), and $\underline{X}$ denotes the reversal of X given by $\underline{X}$=x(N−1−n) for n=0, 1, 2, ..., (N−1). The same is true for Y and $\underline{Y}$.

Figure 10:
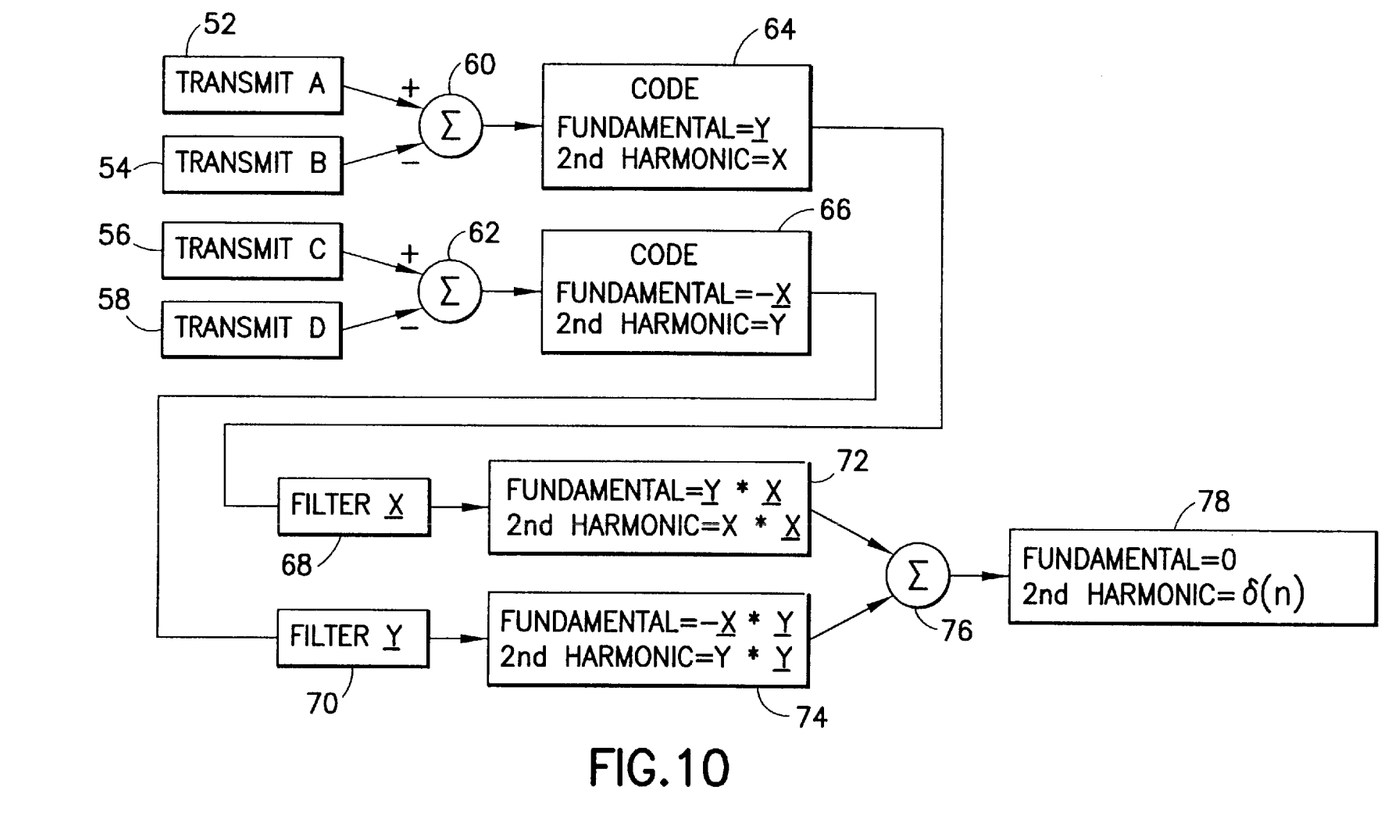
FIG. 10 is a block diagram illustrating a coding and decoding scheme for a Golay code pair [X, Y] in accordance with another preferred embodiment of the invention which utilizes harmonic imaging and four transmits.

FIG. 10 shows the coding and decoding method to achieve fundamental suppression and second harmonic compression for a given Golay code pair X and Y. The received signal 54 from the second transmit B is subtracted from the received signal 52 of the first transmit A in adder/subtracter 60, and the received signal 58 from the fourth transmit D is subtracted from the received signal 56 of the third transmit C in adder subtracter 62 to form the Golay-encoded fundamental and Golay-encoded second harmonic signals (blocks 64 and 66). Formation of the encoded harmonic signal from the difference of two received signals is necessary to equalize the spectra of the second harmonic signals representing the "plus" and "minus" code symbols, since the second harmonic signals generated from different QPSK transmit pulses may not be exactly inverted in phase (e.g., the second harmonic response of the "j" pulse may not be equal to the negative of the second harmonic response of the "1" pulse).

The Golay-encoded harmonic signals are then compressed by matched filtering (filters 68 and 70 in FIG. 10) and summing (summer 76) the filter outputs (blocks 72 and 74 in FIG. 10). With the particular selection of Golay code on the fundamental signal given above, this same filtering and summation cancels the fundamental signal to leave the second harmonic signal for image formation.

To implement the disclosed coding method, four QPSK transmit sequences A, B, C, and D are generated from a given Golay code pair X and Y as follows (where a→b denotes replacing every occurrence of "a" by "b" and the triple product is performed element-by-element):

$$A = X\underline{Y}X(-1 \to j) \quad (1)$$

$$B = X\underline{Y}X(\{1 \to j\}, \{-1 \to 1\}) \quad (2)$$

$$C = -\underline{X}YY(-1 \to j) \quad (3)$$

$$D = -\underline{X}YY(\{1 \to j\}, \{-1 \to 1\}) \quad (4)$$

By using the principles of linear systems, all the required signal differences, filters, and sums shown in FIG. 9 may be condensed for efficient implementation. The received signal 52 from the first transmit A is match filtered with $\underline{X}$, the received signal 54 from the second transmit B is match filtered with $-\underline{X}$, the received signal 56 from the third transmit C is match filtered with $\underline{Y}$, and the received signal 58 from the fourth transmit D is match filtered with $-\underline{Y}$. Finally, all four filtered signals are summed in a vector summer to produce the compressed second harmonic signal with suppressed fundamental signal.

The imaging system incorporating the structure shown in FIG. 9 can also operate by demodulating the RF echo signals to baseband and downsampling before or after beamsummation. In this case, the oversampled sequences would also be demodulated to baseband and downsampled.

Finally, perfusion imaging can also be performed by imaging the second-harmonic signal components in the color flow mode. The traditional color firing sequence is a series of firings (e.g., tone bursts) along the same position, which firings produce the respective receive signals:

$$F_1 F_2 F_3 \ldots F_M$$

where $F_1$ is the receive signal for the i-th firing and M is the number of firings in a packet. These receive signals are loaded into a corner turner memory, and a high pass filter (wall filter) is applied to each down range position across firings, i.e., in "slow time". In the simplest case of a (1, −1) wall filter, each range point will be filtered to produce the respective difference signals:

$$(F_1-F_2)(F_2-F_3)(F_3-F_4) \ldots , (F_{(M-1)}-F_M)$$

and these differences are input to a color flow velocity estimator.

Figure 11:
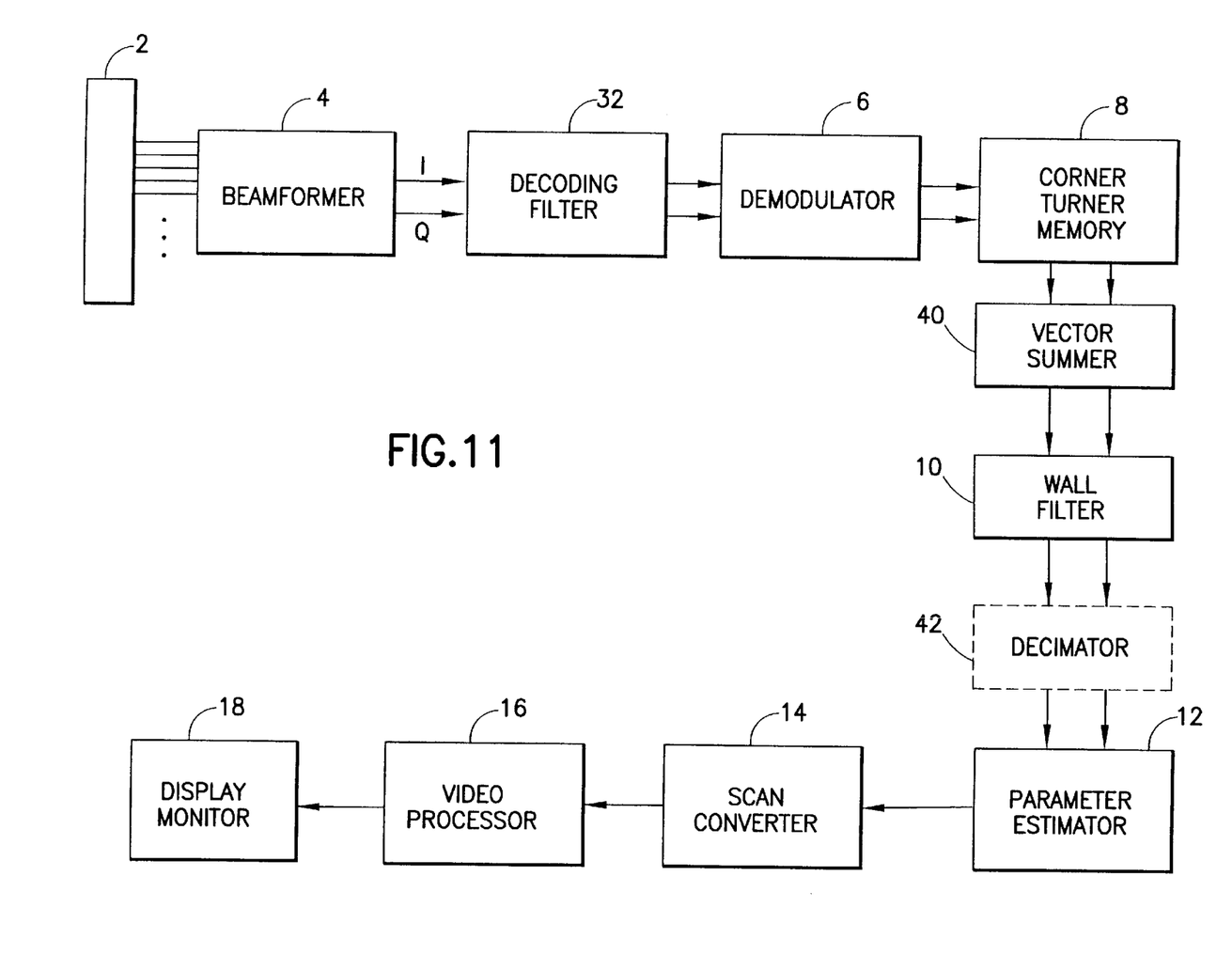
FIG. 11 is a block diagram showing the signal processing chain for a color flow ultrasound imaging system in accordance with another preferred embodiment.

The ultrasound imaging system shown in FIG. 11 employs QPSK code processing for color flow imaging as follows. In accordance with one preferred embodiment, instead of transmitting a packet consisting of M transmit firings (e.g., each pulse being a multi-cycle tone burst), the transducer array transmits a packet consisting of 2M transmit firings, successive transmit pulses being alternatingly encoded with the respective QPSK codes to form alternating encoded pulse waveforms A and B. For example, encoded pulse waveform A could be formed by coding a sequence of n transmit pulse sequences with respective digits of a first n-digit transmit code and coding another sequence of n transmit pulse sequences with respective digits of a second n-digit transmit code, wherein the first and second transmit codes are QPSK codes designed to produce Golay-encoded second-harmonic signals on reception. The autocorrelation is achieved for each transmit firing by loading the decoding filter 32 with a receive code equal to the second-harmonic receive code for that firing and then performing matched filtering of the receive signals. The autocorrelated sequences are then summed using respective dedicated vector summers 40 and high pass filtered using respective wall filters 10. Alternatively, the dual functions of summing Golay code pairs and high pass filtering can be performed by respective "generalized" wall filters. A generalized wall filter is formed by duplicating the filter coefficients of a conventional wall filter. The summed and high-pass-filtered data is optionally decimated by a factor of two in respective decimators 42. The decimated or undecimated data is then input to the parameter estimator 12.

While the invention has been described with reference to preferred embodiments, it will be understood by those skilled in the art that various changes may be made and equivalents may be substituted for elements thereof without departing from the scope of the invention. In addition, many modifications may be made to adapt a particular situation to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A system for transmitting beams of wave energy, comprising:
    a transducer array comprising a multiplicity of transducer elements; and
    a transmitter programmed to activate said transducer array to transmit a bursting pulse waveform in a transmit focal zone during a first transmit firing, said bursting pulse waveform having an amplitude sufficient to burst contrast micro-bubbles in said transmit focal zone, and to transmit a first encoded imaging pulse waveform focused in said transmit focal zone during a second transmit firing subsequent to said first transmit firing.

2. The system as recited in claim 1, wherein said first encoded imaging pulse waveform has an amplitude insufficient to burst contrast micro-bubbles in said transmit focal zone.

3. The system as recited in claim 1, wherein said first encoded imaging pulse waveform is encoded such that a signal component encoded with a Barker code is produced on reception.

4. The system as recited in claim 1, wherein said transmitter is further programmed to activate said transducer array to transmit a second encoded imaging pulse waveform focused in said transmit focal zone during a third transmit firing subsequent to said first transmit firing.

5. The system as recited in claim 4, wherein said first and second encoded imaging pulse waveforms are respectively encoded such that the same signal component in respective receive signals is respectively encoded with first and second Golay codes of a Golay code pair.

6. The system as recited in claim 4, wherein said transmitter is further programmed to activate said transducer array to transmit third and fourth encoded imaging pulse waveforms focused in said transmit focal zone during fourth and fifth transmit firings subsequent to said first transmit firing.

7. The system as recited in claim 6, wherein said first through fourth encoded imaging pulse waveforms are encoded with transmit codes A–D selected such that (A–B) and (C–D) are encoded by $\underline{Y}$ and $-\underline{X}$, respectively, while $(A^2-B^2)$ and $(C^2-D^2)$ are encoded by X and Y, respectively, where X and Y form a Golay code pair, X is a sequence such that X=x(n), n=0, 1, 2, . . . , (N–1), and $\underline{X}$ denotes the reversal of X given by $\underline{X}$=x(N–1–n) for n=0, 1, 2, . . . , (N–1).

8. The system as recited in claim 1, wherein said transducer elements are piezoelectric transducer elements.

9. A method for transmitting beams of wave energy, comprising the steps of:
    activating a transducer array to transmit a bursting pulse waveform in a transmit focal zone during a first transmit firing, said bursting pulse waveform having an amplitude sufficient to burst contrast micro-bubbles in said transmit focal zone; and
    activating said transducer array to transmit a first encoded imaging pulse waveform focused in said transmit focal zone during a second transmit firing subsequent to said first transmit firing, said second transmit firing occurring during refilling of contrast micro-bubbles in said transmit focal zone.

10. The method as recited in claim 9, wherein said first encoded imaging pulse waveform has an amplitude insufficient to burst contrast micro-bubbles in said transmit focal zone.

11. The method as recited in claim 9, wherein said first encoded imaging pulse waveform is encoded such that a signal component encoded with a Barker code is produced on reception.

12. The method as recited in claim 9, further comprising the step of activating said transducer array to transmit a second encoded imaging pulse waveform focused in said transmit focal zone during a third transmit firing subsequent to said first transmit firing, said third transmit firing occurring during refilling of contrast micro-bubbles in said transmit focal zone.

13. The method as recited in claim 12, wherein said first and second encoded imaging pulse waveforms are respectively encoded such that the same signal component in respective receive signals is respectively encoded with first and second Golay codes of a Golay code pair.

14. The method as recited in claim 12, further comprising the steps of activating said transducer array to transmit third and fourth encoded imaging pulse waveforms focused in said transmit focal zone during fourth and fifth transmit firings subsequent to said first transmit firing, said fourth and fifth transmit firings occurring during refilling of contrast micro-bubbles in said transmit focal zone.

15. The method as recited in claim 14, wherein said first through fourth encoded imaging pulse waveforms are encoded with transmit codes A–D selected such that (A–B) and (C–D) are encoded by $\underline{Y}$ and $-\underline{X}$, respectively, while $(A^2-B^2)$ and $(C^2-D^2)$ are encoded by X and Y, respectively, where X and Y form a Golay code pair, X is a sequence such that X=x(n), n=0, 1, 2, ..., (N−1), and $\underline{X}$ denotes the reversal of X given by $\underline{X}$=x(N−1−n) for n=0, 1, 2, ..., (N−1).

16. An imaging system comprising:
a transducer array comprising a multiplicity of transducer elements for transmitting wave energy in response to electrical activation and transducing returned wave energy into electrical signals;
a transmitter programmed to activate said transducer array to transmit a bursting pulse waveform in a transmit focal zone during a first transmit firing, said bursting pulse waveform having an amplitude sufficient to burst contrast micro-bubbles in said transmit focal zone, and to transmit an encoded imaging pulse waveform focused in said transmit focal zone during a second transmit firing subsequent to said first transmit firing, wherein said encoded imaging pulse waveform is encoded using a transmit code;
a receiver programmed to form a receive vector from electrical signals output from selected transducer elements subsequent to said second transmit firing;
a filter for filtering said receive vector to form a compressed pulse vector for a desired signal component; and
a subsystem for displaying an image having an image portion which is a function of said compressed pulse vector.

17. The system as recited in claim 16, wherein said desired signal component is a second harmonic signal component.

18. The system as recited in claim 16, wherein said transmit code is selected such that said receive vector is encoded with a Barker code.

19. The system as recited in claim 16, wherein said transducer elements are piezoelectric transducer elements.

20. An imaging system comprising:
a transducer array comprising a multiplicity of transducer elements for transmitting wave energy in response to electrical activation and transducing returned wave energy into electrical signals;
a transmitter coupled to said transducer array and programmed to activate selected transducer elements to transmit a bursting pulse waveform in a transmit focal zone during a first transmit firing, said bursting pulse waveform having an amplitude sufficient to burst contrast micro-bubbles in said transmit focal zone, and to transmit first and second imaging pulse waveforms during second and third transmit firings subsequent to said first transmit firing, said first and second imaging pulse waveforms being focused in said transmit focal zone and being encoded with first and second transmit codes respectively;
a receiver programmed to form first and second receive vectors from electrical signals output from selected transducer elements subsequent to said second and third transmit firings respectively;
a filter for filtering said first and second receive vectors to form first and second filtered receive vectors for a desired signal component;
a vector summer for summing said first and second filtered receive vectors to form a summed receive vector; and
a subsystem for displaying an image having an image portion which is a function of said summed receive vector.

21. The system as recited in claim 20, wherein said desired signal component is a second harmonic signal component.

22. The system as recited in claim 20, wherein said first and second transmit codes are respectively selected such that said first and second receive vectors are respectively encoded with first and second Golay codes of a Golay code pair.

23. The system as recited in claim 20, wherein said transducer elements are piezoelectric transducer elements.

24. An imaging system comprising:
a transducer array comprising a multiplicity of transducer elements for transmitting wave energy in response to electrical activation and transducing returned wave energy into electrical signals;
a transmitter coupled to said transducer array and programmed to activate selected transducer elements to transmit a bursting pulse waveform in a transmit focal zone during a first transmit firing, said bursting pulse waveform having an amplitude sufficient to burst contrast micro-bubbles in said transmit focal zone, and to transmit first through fourth imaging pulse waveform during second through fifth transmit firings subsequent to said first transmit firing, said first through fourth imaging pulse waveforms being focused in said transmit focal zone and being encoded with first through fourth transmit codes A–D, said transmit codes being selected such that (A–B) and (C–D) are encoded by $\underline{Y}$ and $-\underline{X}$, respectively, while $(A^2-B^2)$ and $(C^2-D^2)$ are encoded by X and Y, respectively, where X and Y form a Golay code pair;
a receiver programmed to form first through fourth receive vectors from electrical signals output from selected transducer elements subsequent to said second through fifth transmit firings respectively;
a matched filter programmed to filter said respective receive vectors as a function of said Golay pair;
a vector summer for summing said filtered receive vectors acquired from said second through fifth transmit firings to form a summed receive vector; and
a subsystem for displaying an image having an image portion which is a function of said summed receive vector.

25. The system as recited in claim 24, wherein said matched filter is programmed with sets of filter coefficients for match filtering said respective receive vectors, said filter coefficient sets comprising $\underline{X}$, $-\underline{X}$, $\underline{Y}$, and $-\underline{Y}$.

26. The system as recited in claim 24, wherein said transmit sequences are encoded using quadrature phase shift keying.

27. An imaging system comprising:
a transducer array comprising a multiplicity of transducer elements for transmitting wave energy in response to electrical activation and transducing returned wave energy into electrical signals;
means for activating selected transducer elements to transmit a bursting pulse waveform in a transmit focal zone, said bursting pulse waveform having an amplitude sufficient to burst contrast micro-bubbles in said transmit focal zone;
means for activating selected transducer elements to transmit at least one encoded imaging pulse waveform subsequent to transmission of said bursting pulse waveform, each imaging pulse waveform being focused in said transmit focal zone;
a receiver programmed to form a respective receive vector from electrical signals output from selected transducer elements subsequent to each transmission of an encoded imaging pulse waveform;

means for decoding said at least one receive vector to form a compressed pulse vector; and a subsystem for displaying an image having an image portion which is a function of said compressed pulse vector.

28. The system as recited in claim 27, wherein said subsystem comprises:

a processing subsystem programmed to form an image signal from said compressed pulse vector; and a display subsystem programmed to display an image having an image portion which is a function of said image signal.

29. An imaging method comprising the steps of:

activating selected transducer elements of a transducer array to transmit a bursting pulse waveform in a transmit focal zone, said bursting pulse waveform having an amplitude sufficient to burst contrast micro-bubbles in said transmit focal zone;

activating selected transducer elements of said transducer array to transmit at least one encoded imaging pulse waveform subsequent to transmission of said bursting pulse waveform, each imaging pulse waveform being focused in said transmit focal zone;

forming a respective receive vector from electrical signals output from selected transducer elements subsequent to each transmission of an encoded imaging pulse waveform;

decoding said respective receive vector(s) to form a compressed pulse vector; and displaying an image having an image portion which is a function of said compressed pulse vector.

30. The method as recited in claim 29, wherein said one encoded imaging pulse waveform is encoded such that a signal component encoded with a Barker code is produced on reception.

31. The method as recited as claim 29, wherein first and second encoded imaging pulse waveforms are respectively encoded such that the same signal component in respective receive signals is respectively encoded with first and second Golay codes of a Golay code pair.

32. The method as recited in claim 29, wherein first through fourth encoded imaging pulse waveforms are encoded using quadrature phase shift keying.

33. The method as recited in claim 29, further comprising the steps of:

injecting contrast micro-bubbles into an anatomical region; and locating said transmit focal zone within said anatomical region.

* * * * *